(12) United States Patent
Ierulli

(10) Patent No.: US 9,730,827 B2
(45) Date of Patent: *Aug. 15, 2017

(54) ECONOMICAL NASAL DILATOR AND METHOD OF MANUFACTURE

(71) Applicant: Corbett Lair, Inc., Bradenton, FL (US)

(72) Inventor: Joseph V. Ierulli, Portland, OR (US)

(73) Assignee: Corbett-Lair Inc., Bradenton, FL (US)

( * ) Notice: Subject to any disclaimer, the term of this patent is extended or adjusted under 35 U.S.C. 154(b) by 863 days.

This patent is subject to a terminal disclaimer.

(21) Appl. No.: 14/042,636

(22) Filed: Sep. 30, 2013

(65) Prior Publication Data

US 2015/0090398 A1 Apr. 2, 2015
US 2017/0112653 A9 Apr. 27, 2017

Related U.S. Application Data

(63) Continuation of application No. 12/024,763, filed on Feb. 1, 2008, now Pat. No. 8,584,671.

(60) Provisional application No. 60/888,543, filed on Feb. 6, 2007.

(51) Int. Cl.

| | |
|---|---|
| B29C 65/48 | (2006.01) |
| B32B 37/12 | (2006.01) |
| B32B 38/04 | (2006.01) |
| B32B 38/10 | (2006.01) |
| B32B 38/18 | (2006.01) |
| A61F 5/08 | (2006.01) |
| B32B 38/00 | (2006.01) |

(52) U.S. Cl.
CPC ............ *A61F 5/08* (2013.01); *B32B 38/0004* (2013.01); *B32B 37/1292* (2013.01); *Y10T 29/49826* (2015.01); *Y10T 83/0524* (2015.04); *Y10T 156/1075* (2015.01)

(58) Field of Classification Search
USPC ....... 156/247–249, 250, 256, 259, 261, 265, 156/271, 289
See application file for complete search history.

(56) References Cited

U.S. PATENT DOCUMENTS

| | | |
|---|---|---|
| 5,476,091 A | 12/1995 | Johnson |
| 5,479,944 A | 1/1996 | Petruson |
| 5,533,499 A | 7/1996 | Johnson |
| 5,533,503 A | 7/1996 | Doubek et al. |
| 5,546,929 A | 8/1996 | Muchin |
| 5,549,103 A | 8/1996 | Johnson |
| RE35,408 E | 12/1996 | Petruson |
| 5,611,333 A | 3/1997 | Johnson |

(Continued)

*Primary Examiner* — Sing P Chan
(74) *Attorney, Agent, or Firm* — Mersenne Law

(57) ABSTRACT

A nasal dilator comprises a laminate of vertically-stacked layers that form a unitary truss. The truss features end regions that engage outer wall tissues of a user's nasal passages, joined by an interconnecting region that traverses the bridge of the nose. The dilator acts to stabilize nasal outer wall tissues and prevent them from drawing inward during breathing. Dilator components are sized and shaped to engage the nose and provide effective dilation, and to facilitate lateral and longitudinal registration during manufacture, while reducing material waste. Methods of manufacture include progressive steps to fabricate and assemble components into finished devices. Some partially-assembled embodiments include a final assembly step performed by the user to create a dilator with a customized truss length.

18 Claims, 10 Drawing Sheets

(56) References Cited

U.S. PATENT DOCUMENTS

| | | |
|---|---|---|
| 5,653,224 A | 8/1997 | Johnson |
| 5,706,800 A | 1/1998 | Cronk et al. |
| 5,718,224 A | 2/1998 | Muchin |
| 5,769,089 A | 6/1998 | Hand et al. |
| 5,842,469 A * | 12/1998 | Rapp .................. A61F 5/08 128/200.24 |
| 5,890,486 A | 4/1999 | Mitra et al. |
| 5,931,854 A | 8/1999 | Dillon |
| 5,957,126 A | 9/1999 | Neeser |
| 6,006,746 A | 12/1999 | Karell |
| 6,029,658 A | 2/2000 | De Voss |
| 6,058,931 A | 5/2000 | Muchin |
| 6,065,470 A | 5/2000 | Van Cromvoirt et al. |
| 6,098,616 A | 8/2000 | Lundy et al. |
| 6,196,228 B1 | 3/2001 | Kreitzer et al. |
| 6,244,265 B1 | 6/2001 | Cronk et al. |
| 6,276,360 B1 | 8/2001 | Cronk et al. |
| 6,318,362 B1 | 11/2001 | Johnson |
| 6,357,436 B1 | 3/2002 | Kreitzer et al. |
| 6,375,667 B1 | 4/2002 | Ruch |
| 6,453,901 B1 | 9/2002 | Ierulli |
| 6,470,883 B1 | 10/2002 | Beaudry |
| 6,550,474 B1 | 4/2003 | Anderson et al. |
| 6,694,970 B2 | 2/2004 | Spinelli et al. |
| 6,769,428 B2 | 8/2004 | Cronk et al. |
| 6,769,429 B1 | 8/2004 | Benetti |
| 7,067,710 B1 | 6/2006 | Beaudry |
| 7,114,495 B2 | 10/2006 | Lockwood, Jr. |
| D639,762 S | 6/2011 | Brogden et al. |
| D644,324 S | 8/2011 | Brunner et al. |
| D644,325 S | 8/2011 | Brunner et al. |
| 8,047,201 B2 | 11/2011 | Guyuron et al. |
| 8,062,329 B2 | 11/2011 | Ierulli |
| D651,710 S | 1/2012 | Brogden et al. |
| 8,115,049 B2 | 2/2012 | Beaudry |
| D659,245 S | 5/2012 | Ierulli |
| 8,188,330 B2 | 5/2012 | Beaudry |
| D662,203 S | 6/2012 | Smith |
| D667,543 S | 9/2012 | Ierulli |
| D671,643 S | 11/2012 | Ierulli |
| D672,461 S | 12/2012 | Brogden et al. |
| D672,872 S | 12/2012 | Brunner et al. |
| D673,270 S | 12/2012 | Brunner et al. |
| 8,342,173 B2 | 1/2013 | Lockwood, Jr. |
| 8,444,670 B2 | 5/2013 | Ierulli |
| 8,459,254 B1 * | 6/2013 | Jassir .................. A61F 5/08 128/200.24 |
| 8,584,671 B2 | 11/2013 | Ierulli |
| 2008/0058858 A1 | 3/2008 | Smith |
| 2008/0097517 A1 | 4/2008 | Holmes et al. |
| 2008/0184995 A1 | 8/2008 | Ierulli |
| 2009/0125052 A1 | 5/2009 | Pinna et al. |
| 2009/0234383 A1 | 9/2009 | Ierulli |
| 2010/0298861 A1 | 11/2010 | Fenton |
| 2011/0000483 A1 | 1/2011 | Matthias et al. |
| 2011/0054517 A1 | 3/2011 | Holmes et al. |
| 2011/0093004 A1 | 4/2011 | Ierulli |
| 2011/0166594 A1 | 7/2011 | Eull |
| 2011/0224717 A1 | 9/2011 | Lockwood |
| 2011/0295312 A1 | 12/2011 | Ierulli |
| 2012/0004683 A1 | 1/2012 | Gray |
| 2012/0022582 A1 | 1/2012 | Guyuron |
| 2012/0067345 A1 | 3/2012 | Shilon |
| 2012/0172923 A1 | 7/2012 | Fenton |
| 2012/0209313 A1 | 8/2012 | Ierulli |
| 2012/0232455 A1 | 9/2012 | Beaudry |
| 2013/0104882 A1 | 5/2013 | Ierulli |
| 2013/0118488 A1 | 5/2013 | Ledogar |

* cited by examiner

ECONOMICAL NASAL DILATOR AND METHOD OF MANUFACTURE

RELATED APPLICATIONS

The present application is a Continuation of, and claims priority benefit to, U.S. Nonprovisional patent application Ser. No. 12/024,763 filed Feb. 1, 2008, incorporated by reference in its entirety herein. U.S. patent application Ser. No. 12/024,763 claims priority benefit to U.S. Provisional Patent Application No. 60/888,543 filed Feb. 6, 2007, also incorporated by reference in its entirety herein.

FIELD OF THE INVENTION

The present invention relates to apparatus and methods of dilating external tissue. As disclosed and taught in the preferred embodiments, the tissue dilator devices and methods of fabrication of tissue dilators are particularly suitable for use as external nasal dilators for supporting, stabilizing, and dilating nasal tissues adjacent and overlying nasal airway passages, including the nasal valve and/or the vestibule areas thereof.

BACKGROUND OF THE INVENTION

A portion of the human population has some malformation of the nasal passages which interferes with breathing, including deviated septa and swelling due to allergic reactions. A portion of the interior nasal passage wall may draw in during inhalation to substantially block the flow of air through the nasal passage. Blockage of the nasal passages as a result of malformation, symptoms of the common cold or seasonal allergies are particularly uncomfortable at night, and can lead to sleep disturbances, irregularities and general discomfort.

Spring-based devices for dilating tissue of the human nose adjacent the nasal passages, and the concept of utilizing resilient means to engage and urge outwardly the nasal passage outer walls from either the interior mucosa or exterior epidermis sides thereof, have a history spanning over one hundred years. Some examples of present external nasal dilators are disclosed in U.S. Pat. Nos. 6,453,901; D379,513; D429,332; D430,295; D432,652; D434,146; D437,64; U.S. patent application Ser. No. 08/855,103; and Japanese patent Reg. No. 1037944; the entire disclosures of which are incorporated by reference herein. The commercial success of at least one of these inventions, together with that of other modern external nasal dilators, collectively and commonly referred to as nasal strips, has led to the creation and establishment of a nasal dilator product category in the present consumer retail marketplace. Commercial success of prior art devices disclosed before 1990 is assumed to be commensurate with the nature of the consumer product retail environments at the times of those inventions.

A long-standing practice in the construction and use of medical devices which engage external bodily tissue (i.e., tissue dilators, nasal splints, ostomy devices, surgical drapes, etc.) is to interpose an interface material between the device and the user's skin to facilitate engagement of the device to the skin and to aid user comfort. Said material, such as a spunlaced polyester nonwoven fabric, typically has properties which permit limited, primarily plastic and somewhat elastic deformation within the thickness thereof. These properties can spread out peeling, separating or delaminating forces such as may be caused by gravity acting on the weight of the device; the device's own spring biasing force or rigidity (such as that of a tissue dilator or nasal splint); biasing force that may be present in bodily tissue engaged by the device; surface configuration differences between the device and the skin of the device wearer; displacement of the device relative to the skin or external tissue as a result of shear, tensile, cleavage and/or peel forces imparted thereat via wearer movement (e.g., facial gestures) and/or contact with an object (e.g., clothing, pillow, bedding, etc.); and so on, that may cause partial or premature detachment of the device from the wearer. By spreading out these delaminating forces, said interface material acts as a buffering agent to prevent the transfer of said forces to its adhesive substance, if any, and thereby to the skin. Preventing the transfer of focused delaminating forces substantially eliminates any itching sensation (caused by the separation of the adhesive substance or device from the skin) that a wearer may experience if these delaminating forces were otherwise imparted directly to the skin.

The present nasal dilator art addresses, in part, obstacles and design constraints of spring-based dilator devices. Firstly, tissues associated with first and second nasal passages have limited skin surface areas to which dilation may be applied. Said surface areas comprise a range extending vertically from the nostril opening to the cartilage just above the nasal valve, and extending horizontally from each approximate line where the nose meets the cheek to the vertical centerline of the bridge of the nose. Secondly, nasal dilators are, of necessity, releasably secured to said skin surfaces by use of pressure sensitive adhesives. Skin surfaces transmit moisture vapor to the surrounding atmosphere. Said adhesives break down in the presence of skin oils, moisture and the transmission of moisture vapor, usually within hours. Thirdly, the functional element of external spring-based nasal dilator devices is a semi-rigid resilient member flexed across and extending on each side of the bridge of the nose adjacent the nasal passages. In modern nasal dilators the resilient member is flat, substantially rectangular or slightly arcuate, and made of plastic. The resilient member exerts a spring biasing force which tends to substantially return or restore the device to an original, typically planar, state thus dilating the local tissue. Fourthly, said spring biasing force creates peel and tensile forces which work to delaminate the end regions of the dilator device from the skin surfaces so engaged. Less than 15 grams of spring return may not provide suitable stabilization or dilation of the nasal passage tissue, while a restoring force of greater than 35 grams would likely be uncomfortable, and would, in addition, require adherence or engagement means that would be uncomfortable, if not damaging, to the tissue.

External nasal dilators are thus subject to the design parameters and dynamics associated with surface area, comfort, dilation efficacy, engagement/adherence means and durational longevity. Accordingly, the vast majority of spring-based nasal dilator devices which engage nasal outer wall tissues are typically within 5.0 to 7.5 cm (2.0" to 3.0") in length and 1.2 to 2.5 cm (0.5" to 1.0") in width. Their resilient members are typically from 4.2 to 5.8 cm (1.7" to 2.3") long, approximately 0.048 to 0.12 cm (0.12" to 0.30") wide and typically 0.010" thick. A resilient member thickness of more or less than 0.010" is not typically used in the art, but can be incorporated with proportionate adjustments to width and length.

The most widely used peripheral dimensions of commercially available nasal strip devices result in material usage (excluding resilient member material) of about 1.7" squared (from an average 2.63"L×average 0.63"W), and up to about 3.3" squared if two full dimensional material layers are used.

The latter is considered a best practice for commercially available nasal strips. Nasal strips are typically manufactured in a continuous process with their lengths parallel to the machine direction (MD) of the material used. Standard converting techniques space each strip apart by about 0.125" on all sides to allow waste material therebetween to be removed as a single matrix. To individually package finished dilators in the same operation, said spacing must be further increased to allow a suitable contact perimeter extending around the dilator within which upper and lower packaging material webs may form a seal. Individual packaging is also considered a best practice. In the alternative, nasal strip parts fabricated in closer proximity with correspondingly less waste may be individually packaged in a separate operation, with an additional converting cost associated therewith, in lieu of said additional spacing between nasal strip devices. Regardless, material usage in a spaced-apart relationship, excluding resilient member material, can be substantially in excess of that which is devoted to the dilator itself, and can encompass about 3.9" squared (3.13"L×1.25"W) per each of one or two layers. Accordingly, 1,000 square inches (MSI) of material could yield as few as about 256 single-layer, substantially rectangular, dilator devices that are narrower in the middle and wider at their ends, or about 128 two-layer devices (dilator material use=256×1.7" sq., or 128×3.3" sq. per MSI). This corresponds to material usage of about 43% with a corresponding waste of about 57%, or a usage-to-waste ratio of about 0.75 to 1.

A minority of presently known nasal dilator devices are suitable or adaptable for mass commercialization in the present consumer retail markets. A minority of these have had commercial success. Exemplary of the latter include devices disclosed in U.S. Pat. Nos. D379,513; 5,546,929; RE35408; 7,114,495; Spanish Utility Model 289-561 for Orthopaedic Adhesive; and a widely available retail product, Breathe Right Nasal Strips. These devices provide sufficient dilation of nasal passageway tissue and thus provide the claimed benefit to the vast majority of users. However, these devices can be costly to manufacture, either by wasting material in the course of manufacture and packaging, or by greater fabrication (i.e., converting) costs associated with techniques by which to reduce material waste. Furthermore, these devices are not adapted for assembly of their constituent components by the user.

In an open market environment, nasal dilator device innovation and competitive value propositions to resellers and consumers contribute to product category viability and longevity. A need in the art thus exists for continued innovation in manufacturing nasal dilator devices at lower costs without sacrificing features that may adversely affect user perception of device benefits or measurable device efficacy. The present invention is directed to discrete embodiments and various forms of external nasal dilators, including techniques and methods for manufacturing nasal dilators and/or fabricating the constituent components thereof.

SUMMARY OF THE INVENTION

The present invention teaches, depicts, enables, illustrates, describes and claims new, useful and non-obvious apparatus and methods of providing dilation to external tissue. In particular, the present invention provides a wide variety of tissue dilators adapted to engage an exterior tissue region of a nose to dilate interior nasal passages thereof, including the vestibule and/or nasal valve areas. The present invention builds upon the prior art and addresses several still unmet needs in the art.

In the specification and claims herein, the term vertical refers to a direction parallel to the thickness of the dilator or truss. The term horizontal refers to a direction parallel to the length, or longitudinal extent, or long axis of the dilator or truss. The term lateral refers to the width or opposite end edges of the dilator or truss, or a direction perpendicular to the length, longitudinal extent, or long axis of the dilator or truss. The term longitudinal centerline refers to a line parallel to the longitudinal extent of the dilator or truss, bisecting the width of the dilator or truss midway between its upper and lower long edges. The term lateral centerline refers to a line perpendicular to the length, longitudinal extent, or long axis of the dilator or truss, bisecting the long axis, or upper and lower long edges, midway along the length thereof.

The external nasal dilator of the present invention comprises a laminate of vertically stacked layers, each comprising at least one member which may include components thereof, including a base layer, a resilient layer comprising resilient means, and a cover layer. The combined laminated layers form a unitary, or single body, truss. The truss features horizontal regions including first and second end regions adapted to engage outer wall tissues of first and second nasal passages, respectively, and an intermediate region adapted to traverse a portion of a nose located between the first and second nasal passages and joining the end regions. In use the dilator acts to stabilize and/or expand the nasal outer wall tissues and prevent said tissues from drawing inward during breathing.

Dilator members and/or components are fabricated to dimensional criteria suitable to engage and provide effective dilation to nasal passages, as described hereinbefore, that create lateral and longitudinal registration of dilator members or components during manufacture, and that facilitate manufacture with minimal material waste, all as part of a continuous manufacturing process. The dilator of the present invention is configured to maximize the percentage of a given amount of material used in the manufacturing process and to return a greater number of individual dilator units per a given quantity of material. The dilator is further configured to facilitate assembly and application by the user (i.e., fabricated in situ) and to allow user adjustment of the truss length. The truss is configured to be comfortable on the tissue engaged and to be easily removed from the tissue with minimal stress thereto.

Methods of manufacture include separate functions, or steps, for the fabrication, assembly and packaging of dilator members and/or components thereof. Said functions or steps are combined into a single continuous process. Embodiments include, without limitation, a truss which features a resilient member with divergent extensions and/or enlarged terminal ends, resilient means comprising a plurality of resilient members joined together at their end portions to form a single member, and a truss adapted for user-adjusted length thereof.

It is the principal objective of this invention to provide nasal dilator devices which overcome the aforementioned limitations and disadvantages of prior dilator devices. It is a further objective of this invention to provide nasal dilator devices that are less expensive to manufacture, that utilize a greater percentage of a given quantity of material in the manufacturing process without increasing the converting cost thereof, that are simple and easy to use, that use less material in device construction, that waste less material in manufacturing, that effectively dilate external tissue, that may be assembled by the user, that have a user-adjustable length, that are comfortable and may be removed from the tissue with minimal stress thereto, and which are more affordable to the user than prior art dilator devices.

For fabricating and assembling the dilator of the present invention, the skilled man in the art will appreciate the applicability of the continually developing art of medical device converting, including rotary laminating and die cutting, flatbed and class A tool die cutting and punching, fluid or pneumatic modular automation components, and pneumatic feeding and material handling components and systems.

The present invention is not limited to the illustrated or described embodiments as these are intended to assist the reader in understanding the subject matter of the invention. The preferred embodiments are examples of forms of the invention comprehended by the devices taught, enabled, described, illustrated and claimed herein. All structures and methods which embody similar functionality are intended to be covered hereby. In certain instances, the devices depicted, taught, enabled and disclosed herein represent families of new, useful and non-obvious tissue dilators having a variety of alternate embodiments. The skilled man will appreciate that features, devices, elements, components, methods, processes or techniques may be applied, interchanged or combined from one embodiment to another. Dilator members, components, materials, layers or regions may be of differing size, area, thickness, length or shape than that illustrated or described while still remaining within the purview and scope of the present invention. The preferred embodiments include, without limitation, the following numbered, discrete forms of the invention, as more fully described below.

BRIEF DESCRIPTION OF THE SEVERAL VIEWS OF THE DRAWING

In the drawings which accompany this disclosure, like elements are referred to with common reference numerals. Drawings are not rendered to scale.

DETAILED DESCRIPTION OF THE INVENTION

Figure 1:
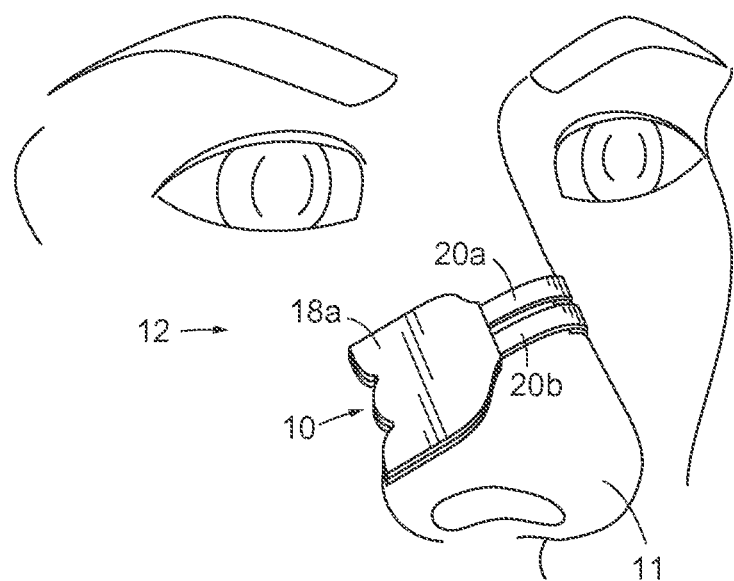
FIG. 1 is perspective view of a portion of a face with a nasal dilator in accordance with the present invention secured to a nose.

An embodiment of nasal dilator, 10, in accordance with the present invention, is illustrated in FIG. 1 which shows dilator 10 engaged to a nose, 11, seen as a portion of a human face, 12.

Figure 2:
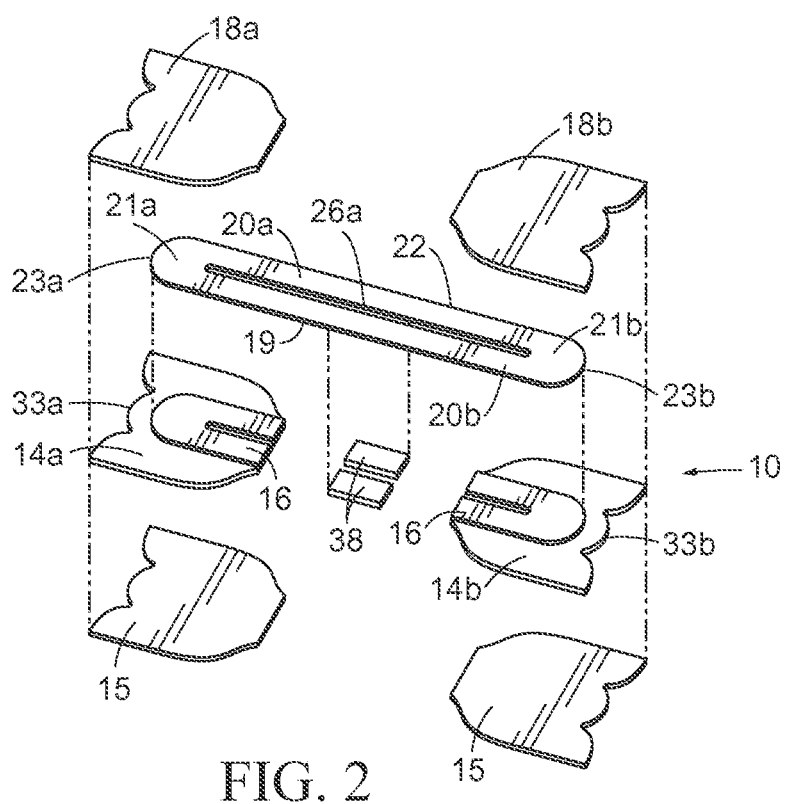
FIG. 2 is an exploded perspective view of the nasal dilator of FIG. 1.

As illustrated in FIG. 2, dilator 10 comprises a laminate of vertically stacked layers, each comprising at least one member which may include components thereof, including: a base layer composed of discrete first and second base layer pads, 14a, and 14b, which may be formed as a single member; a resilient layer composed of a pair of spaced apart upper and lower resilient bands, 20a and 20b joined together at end portions, 21a, and 21b, respectively, to form a single resilient member, 22; and a cover layer composed of discrete first and second cover layer pads, 18a and 18b, which may be formed as a single member. First and second cover layer pads 18a and 18b may have like or dissimilar dimensions as first and second base layer pads, 14a and 14b. A protective layer of release paper liner, 15, removably covers the exposed adhesive of base layer pads 14a and 14b preliminary to use of dilator 10. The shape and dimensions of release liner 15 may correspond to the periphery of base layer pads 14a and 14b, the periphery of dilator 10, or a periphery exceeding one or more dilators 10. The members, components or layers of dilator 10 are not required to be, but are preferably, aligned along their longitudinal centers. Said longitudinal centers are parallel to the length, or longitudinal extent, of dilator 10.

The preferred material for the base and cover layers is from a group of widely available flexible nonwoven synthetic fabrics that allows the skin on user nose 11 to exchange gases with the atmosphere and to maximize comfort of dilator 10 thereon. Said fabrics have a continuous pressure sensitive adhesive substance disposed on one flat surface side thereof; the adhesive side, opposite the non-adhesive side. The non-adhesive side is opposite the skin facing/engaging side. Said adhesive is preferably of a type that is biocompatible with external human tissue for engaging dilator 10 to the nose 11 of a wearer. A protective layer of release paper liner removably covers said adhesive. Said fabrics are available in continuous rolls wound in a machine direction (MD) or warp, which is perpendicular to the cross direction (XD) or fill, of the fabric. The members, components and layers of dilator 10 may be fabricated parallel to either the warp or the fill of said fabrics. Base layer pads 14*a* and 14*b* and/or cover layer pads 18*a* and 18*b* are configured by their length and width to correspond to at least portions of the skin surfaces of outer wall tissues adjacent and overlying first and second nasal passages, respectively. As described hereinbefore, said surfaces extend vertically from the nostril opening to just above the nasal valve and extend horizontally from the approximate lines where nose 11 meets the cheek of a face 12 to the vertical centerline of the bridge of nose 11. The width of first and second base layer pads 14*a* and 14*b* and/or the first and second cover layer pads 18*a* and 18*b* define the width of dilator 10.

An interface member, 16, may be optionally interposed between at least portions of the layers of dilator 10, but preferably between the base layer and resilient layers. Interface member 16 may comprise an adhesive substance or a suitable material, including flexible or semi-rigid plastic, fabric, foam or the like with an adhesive substance disposed at least in part on either one or both opposite flat surface sides. Interface member 16 may be of any shape, but preferably does not exceed the periphery of dilator 10. Interface member 16 may optionally extend along the entire length of resilient member 22 or a portion thereof. FIG. 2 shows interface member 16 joining or laminating the resilient layer to the base layer. It may simultaneously laminate portions of the base layer to the cover layer.

Figure 3:
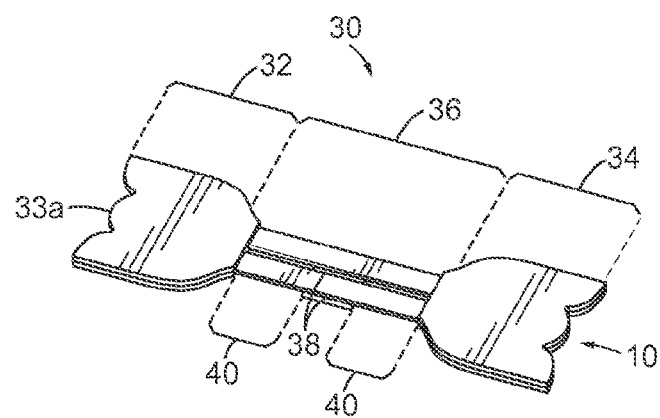
FIG. 3 is a perspective view of the nasal dilator of FIG. 2.

The preferred material from which resilient member 22 is fabricated is a biaxially oriented polyester resin (PET) widely available in continuous rolls under trade names such as Mylar® and Melinex®. Said rolls may include a continuous pressure sensitive adhesive substance disposed on one flat surface side thereof protected by a layer of release paper liner which removably covers said adhesive. PET comes in standard thicknesses of 0.005", 0.007", and 0.010". The spring biasing properties of PET are similar both MD and XD. Accordingly, in the preferred embodiments herein, resilient member components are preferably fabricated perpendicular to the continuous roll length (MD) of the PET. Resilient member 22 may have an adhesive substance disposed on at least a portion of at least one of two opposite flat surface sides for engaging or laminating resilient member 22 to other members, components or layers of dilator 10 as well as to the skin of nose 11. Optionally eliminating adhesive from along those portions or surfaces of resilient member 22 that contact the skin of a nose 11 creates and defines an adhesive void, 19, along said contacting portions or skin-facing surfaces. With less adhesive surface on dilator 10, adhesive void 19 allows easier removal from nose 11 with less stress thereto. Resilient member 22 has opposite terminal ends, 23*a* and 23*b*, respectively, that may conform to at least portions of the outer lateral end edges of dilator 10. Terminal ends 23*a* and 23*b* may be variably aligned with said end edges, extending past or short thereof. In this manner the overall length of truss 30 may be increased or decreased to fit a wider range of dimensions of a nose 11 without altering the spring biasing properties of resilient member 22. As illustrated in FIGS. 1-3, terminal ends 23*a* and 23*b* of resilient member 22 are preferably rounded and preferably correspond to at least portions of like rounded outer lateral end edges of dilator 10.

Resilient member 22 includes a discontinuity of material in the form of a material separation which may be contained either wholly within the peripheral edges of resilient member 22, or may extend inward or outward from at least one peripheral edge thereof. Said material separation may comprise at least one slit, cut, opening, notch, protrusion, indentation or the like, and may be symmetric, asymmetric, straight, curved or gradient. In FIGS. 1-5, said material separation comprises an elongated interior opening, 26*a*, extending along the length of resilient member 22. Opening 26*a* defines the parallel, spaced apart relationship of upper and lower resilient bands 20*a* and 20*b*, and defines the lengths of first and second end portions, 21*a* and 21*b*, of resilient member 22. First and second end portions 21*a* and 21*b* extend from each terminal end of opening 26*a* to each terminal end 23*a*, 23*b*, respectively, of resilient member 22. End portions 21*a* and 21*b* may be of the same or dissimilar widths as the overall width of resilient member 22. Resilient bands 20*a* and 20*b* may be of like or dissimilar widths, and are preferably parallel to each other and parallel to a longitudinal extent of dilator 10. The spaced apart arrangement of resilient bands 20*a* and 20*b*, along with the relatively slight thickness of the PET, enhances the axial, torsional flexibility of resilient member 22 along its length.

Resilient member 22 is configured by its overall dimensions of width, length, and thickness to provide between 15 and 30 grams of spring return biasing force. In those embodiments where resilient member 22 includes a upper and lower resilient bands, 20*a* and 20*b*, each band contributes a portion of that total. Thus the dimensions of resilient member 22, which may be defined in part by opening 26*a*, end portions 21*a* and 21*b*, and upper and lower resilient bands 20*a* and 20*b*, determine said spring biasing force and further define the lateral and longitudinal dimensional relationships of resilient member 22 to the other components of dilator 10.

As illustrated in FIG. 3, the combined laminated layers of dilator 10 create, define and form a unitary, or single body, truss, 30, having horizontal regions as indicated by broken lines. Truss 30 includes a first end region, 32, a second end region, 34, and an intermediate region, 36, joining first end region 32 to second end region 34. The members or components of dilator 10 may overlap from the originating region to the adjacent region. End regions 32 and 34 are adapted to engage outer wall tissues of first and second nasal passages, respectively. Discrete base layer pads 14*a* and 14*b* and/or discrete first and second cover layer pads, 18*a* and 18*b*, correspond substantially to respective first and second end regions 32 and 34. Accordingly, said discrete cover or base layer pads may be referred to generally as end region components.

End regions 32 and 34 include lateral end edges, 33*a*, and 33*b*, respectively, which typically define the outer lateral end edges of truss 30 and thus dilator 10. End edges 33*a* and 33*b* may correspond or conform, at least in part, to terminal ends 23*a* and 23*b* of resilient member 22. The width of intermediate region 36 is generally less than the width of end regions 32 and 34, and may be prevented from contacting the skin by use of a centrally located absorbent pad, 38. Pad 38 creates and defines a contact void, 40, between the skin facing side of intermediate region 36 and the skin of the nose 11, and extending from the lateral sides of pad 38 to respective end regions 32 and 34. As with adhesive void 19, contact void 40 aids in user comfort due the truss 30 contacting less of the skin surface area of a nose 11 than would otherwise be engaged by dilator 10. Thus dilator 10 may be more easily removed from the tissue with less stress thereto.

When engaged to a nose 11, dilator 10, through its resilient means and as a result of its constituent members, components and layers combined to form truss 30, acts to stabilize and/or expand the nasal outer wall tissues and prevent said tissues from drawing inward during breathing.

Figure 4:
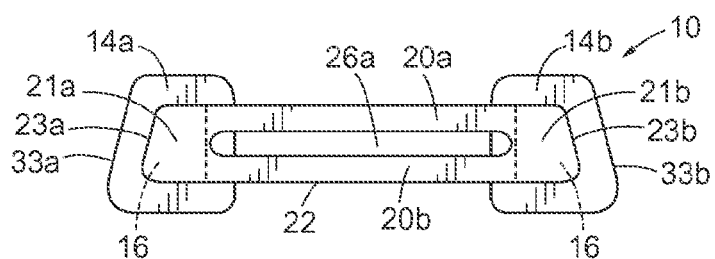
FIG. 4 is a plan view of a second form of nasal dilator embodying the features of the present invention.

FIG. 4 illustrates an alternative form of the nasal dilator of FIGS. 1-3 in which terminal ends 23a, and 23b of resilient member 22 are substantially straight and are angled inward in a direction from bottom to top, corresponding substantially to like angled lateral end edges 33a and 33b of truss 30. A cover layer is optional.

Dilator members and/or components are fabricated to dimensional criteria including: (a), dimensions suitable for engaging and providing effective dilation to nasal outer wall tissues within design parameters as described hereinbefore; (b), dimensions whereby individual dilator members or components thereof are continuously fabricated in close proximity to one another and/or along common lines that define at least a portion of their peripheral edges; and (c), dimensions that create lateral and longitudinal registration of dilator members or components thereof to their respective layers and to each other as part of a continuous fabrication process.

Said registration is achieved during manufacturing by aligning a repeating ratio of a first member, or its components, from a continuous succession thereof, to a repeating ratio of a second member or its components, from a continuous succession thereof, thereby forming at least one layer of the dilator. As more particularly discussed below, successive resilient members are laminated to continuous end region components, optionally via interface member 16, by registered laterally to successive rows of end region components and registered longitudinally to corresponding pairs of end region components.

Figure 5:
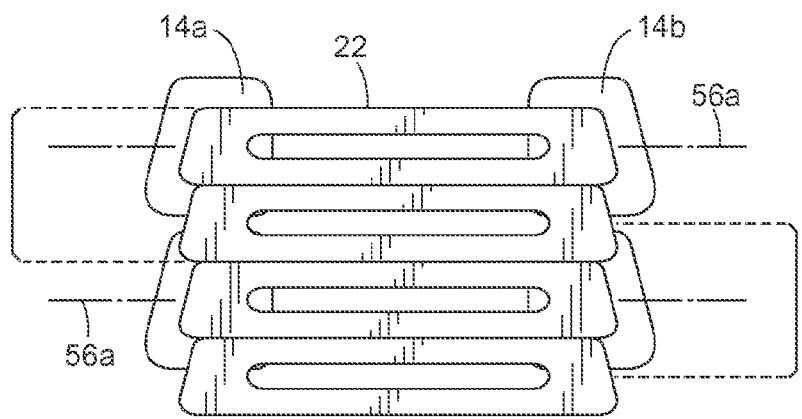
FIG. 5 is a fragmentary plan view illustrating lateral registration, within a continuous fabrication process, of components of the nasal dilator of FIG. 4.

FIG. 5 illustrates lateral registration of separate dilator components as part of a continuous fabrication process whereby to form at least one layer of dilator 10. Continuous resilient member components are die cut from, and perpendicular to, the length (MD) of a continuous web of resilient layer material to form continuous resilient members aligned along common long edges. Continuous end region components are similarly die cut from a continuous material web, optionally spaced apart adjacent their respective long edges, to form continuous successive pairs thereof. The combined widths of a greater number of continuous resilient member components correspond to the combined widths of a lesser number of continuous successive pairs of end region components (shown in broken lines and brackets) such that the longitudinal centerline of at least one resilient member 22, out of consecutive equal numbers thereof, registers to each successive pair of end region components, preferably along the longitudinal centerline, 56a, thereof. In this case the combined width of two successive resilient members (or any multiple thereof) equals the width of a corresponding end region component, or pair (or any multiple thereof), optionally plus spacing, if any, between successive end region components, a ratio of 2:1. Furthermore, the registration ratio of the continuous resilient member components is 1:2 (one out of each two successive parts is registered), and the registration ratio of the (pairs of) end region components registered thereto is 1:1 (each successive pair is registered to).

It will be obvious to the skilled man that a range of registration ratios between any two disparate continuous dilator members (including components thereof) is possible while keeping within the teachings of the present invention. It will be further obvious that while centerline alignment provides a symmetric dilator, it is not a requirement. An asymmetric dilator may be formed using the same technique by aligning members or components off center.

Figure 6:
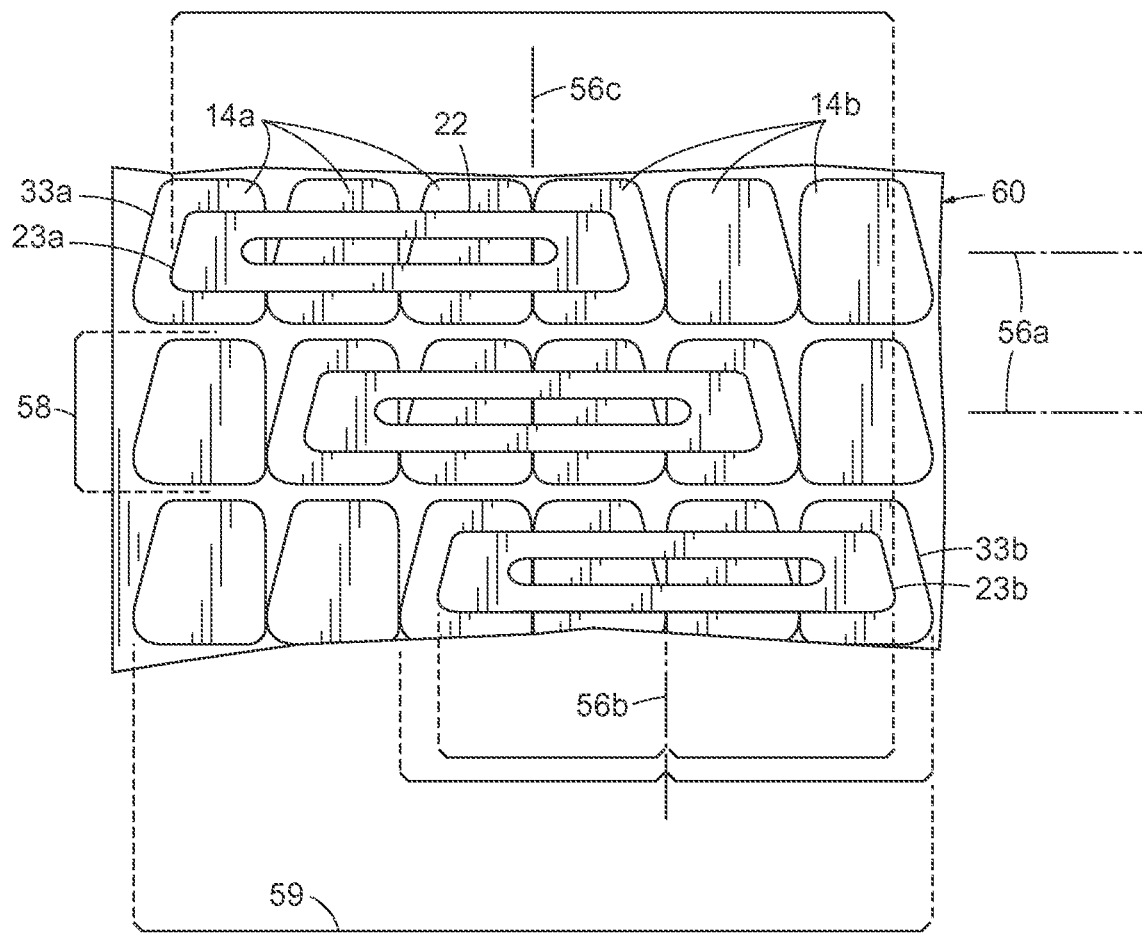
FIG. 6 is a fragmentary plan view illustrating longitudinal registration, within a continuous fabrication process, of components of the nasal dilator of FIG. 4.

FIG. 6 illustrates, in broken lines and brackets, longitudinal registration of separate dilator members to form at least one layer of dilator 10. The combined lengths of a greater number of end region components within successive rows align with the combined overlapping lengths of a lesser number of successive resilient members such that each overlapping resilient member, within successive rows thereof, aligns horizontally with the lateral centerline, 56b, of successive pairs of first and second end region components. For the sake of clarity, FIG. 6 shows resilient members 22 horizontally staggered across said successive rows of end region components. However, FIG. 7 more particularly illustrates said continuous overlapping resilient members in broken lines. The ratio of said longitudinal registration is 1:1. That is, each resilient member is registered to each pair of end region components.

Figure 7:
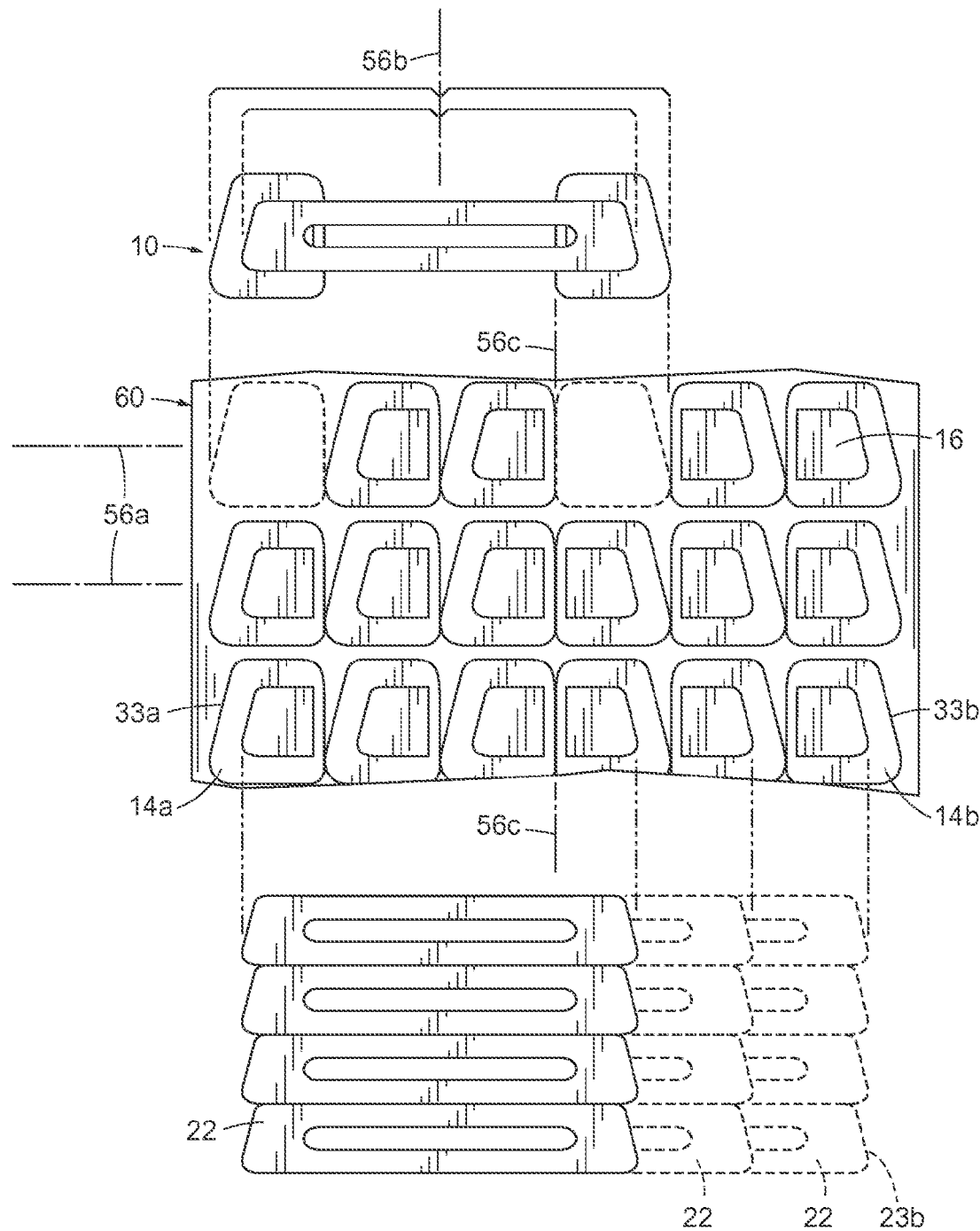
FIG. 7 is a fragmentary plan view illustrating a method of manufacturing and assembling constituent layers of the nasal dilator of FIG. 4.

FIGS. 6-7 further illustrate registration of dilator components as part of a continuous fabrication process. Continuous base layer pads 14a and 14b are die cut in successive rows, 58, from continuous material web 60 in a cross direction (XD) perpendicular to the machine direction (MD) of said material. Since end region components corresponding to respective first and second nasal passages are typically mirror images of each other, rows 58 contain an equal number of base layer pads 14a die cut across from an equal number of base layer pads 14b, forming a group, 59, aligned along their longitudinal centerlines 56a. Group 59 is horizontally centered on a lateral centerline, 56c, which is perpendicular to centerline 56a. Accordingly, the first of said equal number of base layer pads 14a within group 59 corresponds to the first of said equal number of base layer pads 14b. Second of, and third of, base layer pads 14a further correspond to second of and third of base layer pads 14b (and optionally so on). Each row 58 thus has at least one group 59 of corresponding pairs of base layer pads aligned to centerlines 56a and 56c. Each of said pairs substantially defines the length of dilator 10 and first and second end regions 32 and 34 of truss 30. The number of groups 59 within each row 58 are limited only be the width (XD) of web 60.

FIG. 7 also illustrates that web 60 may optionally include interface members 16 laminated thereto in a spaced apart grid, each member 16 registering with each end region component in groups 59 of rows 58 for laminating end portions 21a and 21b of resilient member 22. As further shown in FIG. 7, three overlapping sets of continuous resilient members 22 are laminated to groups 59 within rows 58. Accordingly, successive steps must be used to laminate one set at a time, and the resultant laminates extracted from the material matrix so as to expose the end region components underneath, before proceeding to subsequent overlapping sets of continuous resilient members. Said extraction may be accomplished, for example, by pneumatic suction removal of the finished parts (i.e., a "pick and place" motion control system) from the material web. The extracted parts may be placed on a separate continuous release paper liner, and groups thereof packaged for retail sale. In addition, said grid of interface members 16 may be optionally laminated to the continuous resilient layer material in the course of fabricating resilient members 22.

As further illustrated in FIGS. 6-7, the inside lateral edges of said third of base layer pads 14a and said first of base layer pads 14b lie, at least in part, adjacent to line 56c. Said edges may also align directly on line 56c. The number of base layer pads in group(s) 59, of row(s) 58, is determined by their shape and dimensions, preferably configured, along with the dimensions of resilient member 22, to engage and provide effective dilation to a nose 11 within design parameters as discussed hereinbefore; said shape and dimensions being thus limited by said design parameters. Base layer pads 14*a* and 14*b* fabricated from web 60 in close proximity to one another as shown in FIGS. 6-7 utilize about 70% of the surface area of web 60. The corresponding material waste is thus about 30%, providing a usage-to-waste ratio of about 2.33:1. In the embodiments of FIGS. 4-7, a cover layer for dilator 10 is optional; the adhesive substance on resilient members 22 and/or interface members 16 being sufficiently strong so as to maintain the structural integrity of truss 30 when dilator 10 is in use on a nose 11.

Figure 8:
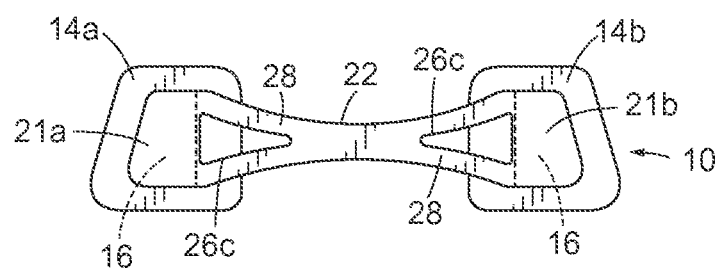
FIG. 8 is a plan view of a third form of nasal dilator embodying the features of the present invention.

FIG. 8 illustrates an embodiment in accordance with the present invention based upon the peripheral dimensions of the dilator of FIG. 4, in which the discontinuity of material of resilient member 22 comprises two openings 26*c*, one on each side of the lateral centerline of truss 30. Openings 26*c* extend from intermediate region 36 into end regions 32 and 34, respectively, forming upper and lower spring fingers 28 which terminate at end portions 21*a* and 21*b*, respectively, of resilient member 22. At least a portion of resilient member 22 has a continuous gradient width, which may curve arcuately or be straight, and is narrower at intermediate region 36 and wider at end regions 32 and 34. Openings 26*c* may be used to laterally spread the spring biasing properties of dilator resilient means primarily at the end regions of the truss. Openings 26*c* may also gradiently reduce spring biasing properties in horizontal direction extending from the intermediate region to opposite end edges 33*a* and 33*b*, respectively. Interface members 16 may be interposed between end portions 21*a* and 21*b* and base layer pads 14*a* and 14*b*, respectively, the inside lateral edges thereof represented by broken lines.

Figure 9:
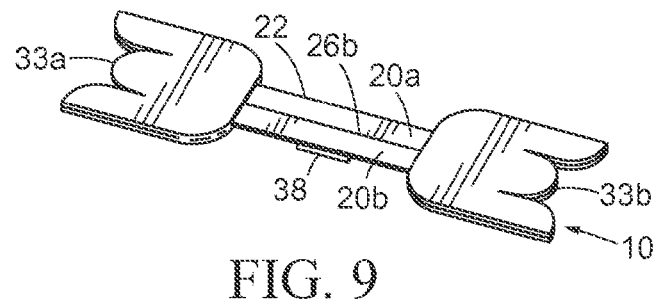
FIG. 9 is a perspective view of an alternative form of nasal dilator embodying the features of the present invention.

FIG. 9 illustrates an alternative nasal dilator 10 in accordance with the present invention in which the material separation of resilient member 22 comprises an elongated interior slit, 26*b*, extending along the length thereof. Similar to opening 26*a*, slit 26*b* defines, at least in part, the widths of upper and lower resilient bands 20*a* and 20*b*, the spaced apart relationship thereof, and the lengths of first and second end portions, 21*a* and 21*b*, of resilient member 22.

Figure 10A:
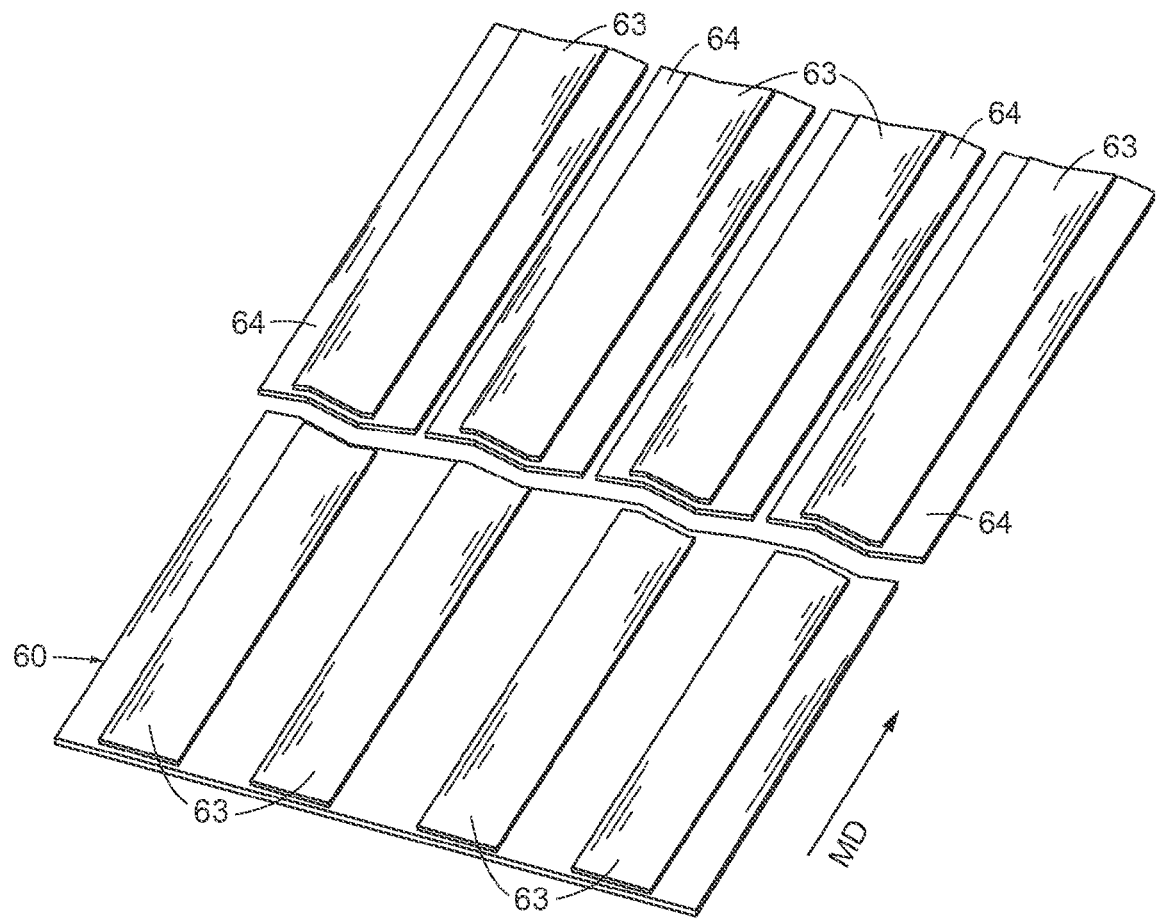
FIG. 10a is a fragmentary perspective view illustrating the initial steps of a method of manufacturing a nasal dilator.

FIG. 10*a* illustrates the initial steps of a continuous fabrication process (using the dilator of FIG. 9 as an example) in which continuous strips of interface material, 63, are laminated onto the non-adhesive side of continuous base layer material web 60 at spaced apart intervals across (XD) web 60. The width of continuous material strips 63 may be varying or constant, but in either case defines the length of interface member 16. Said length is parallel to the longitudinal extent of truss 30. Web 60 is then slit lengthwise (MD) into continuous strands, 64, with each strand 64 including one continuous strip 63 laminated thereto. The widths of continuous material strands 64 may be varying, constant or gradient, but in any case defining the length of base layer pads 14*a* and 14*b*, said length being parallel to the longitudinal extent of truss 30. In addition, the placement of said slits and resultant width of each strand 64 generally correspond to respective end regions of truss 30. Said placement of slits and resultant widths, whether varying, gradient or straight, is preferably substantially uniform, but may be optionally non-uniform.

Figure 10B:
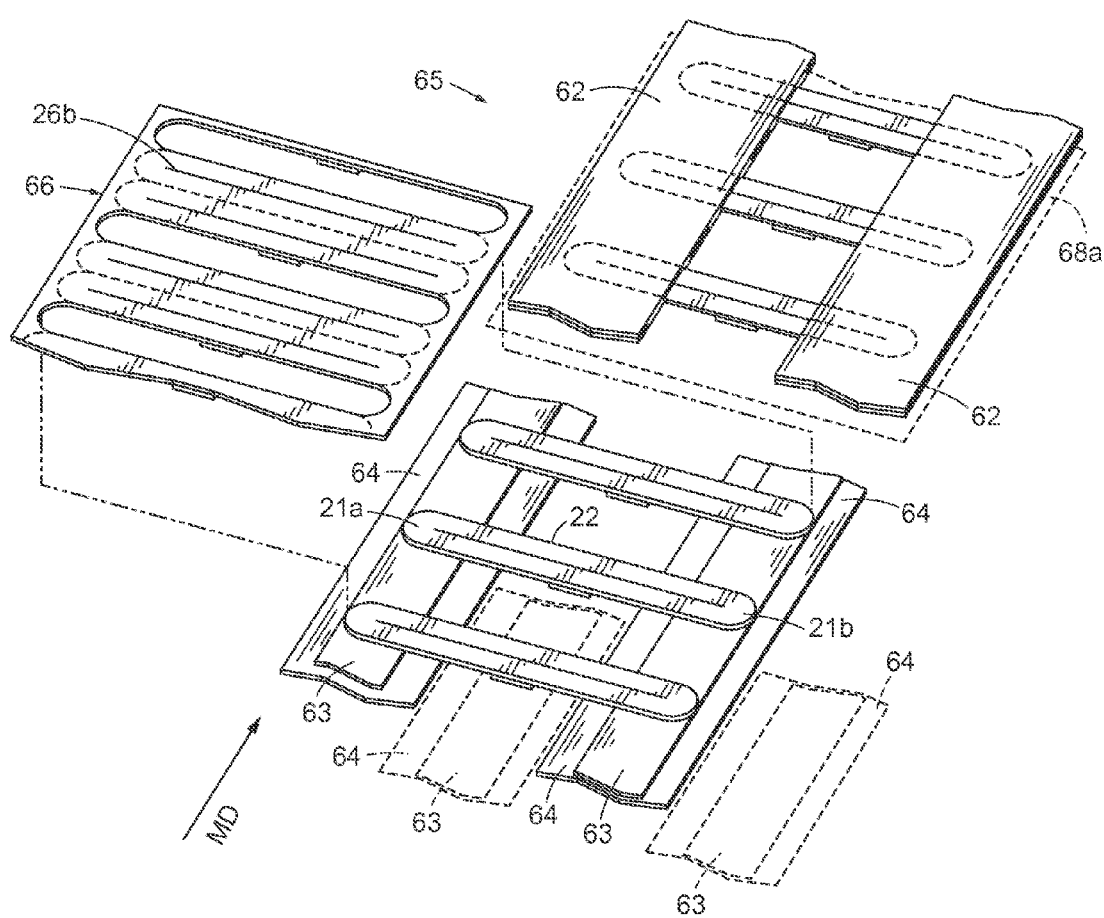
FIG. 10b is a fragmentary perspective view illustrating subsequent steps of a method of manufacturing the nasal dilator of FIG. 9.

FIG. 10*b* continues the fabrication process. Every other strand 64, while maintaining their relative positions, is grouped as a pair forming the base of a fabrication matrix, 65. Said pair may be optionally rewound onto a separate continuous release paper liner to releasably secure both strands 64. This requires separating base layer material 60 from its original protective release paper liner in the course of slitting strands 64. The width of each strand 64 and the spacing between each strand in a pair corresponds substantially to the lengths of first, second and intermediate regions of truss 30. The inside edge of each strand 64 within a pair thereof defines the inside lateral edges of base layer pads 14*a* and 14*b*.

A continuous strand of material from which pad 38 will be formed is preferably laminated to the adhesive side of a continuous resilient layer material web, 66. Web 66 is then aligned and its speed and machine direction synchronized to the fabrication matrix base so as to allow lateral registration of at least one resilient member 22, out of consecutive equally numbered groups thereof, to be die cut from resilient material web 66 and laminated onto the fabrication matrix base at equally spaced apart intervals thereon, thus further forming fabrication matrix 65. Material separation 26*b* is formed at the same time. Said intervals preferably correspond to the longitudinal centerline of dilator 10 plus the width of dilator 10 extending laterally from both sides of said centerline, plus any desired spacing between dilators 10 die cut from fabrication matrix 65. Said placement further defines the point of contact for end portions 21*a* and 21*b* of resilient member 22 to base layer pads 14*a* and 14*b* via interface member 16. In this case, the lateral registration ratio of the continuous resilient member components is 1:3 (one out of each three successive parts is registered). It will be apparent to the skilled medical device converter that, as an alternative to dimension-based lateral registration of dilator components or members (where, for example, the combined widths of x like components corresponds to the width or widths of a disparate component), synchronizing separate material webs by using different machine speeds may also be used to align disparate dilator members or components.

FIG. 10*b* further illustrates a pair of continuous cover layer material strands, 62, laminated onto fabrication matrix 65 via their adhesive sides, substantially over the non-adhesive sides of strands 64. Alternatively, a single strand 62, preferably not greatly exceeding the width of fabrication matrix 65, may be laminated thereto. Strand 62 may be of any width, and may be laminated off-center strands 64 or fabrication matrix 65, and may thus further define the length of truss 30 or may cause end regions 32 and 34 to overlap into intermediate region 36 when dilator 10 is die cut therefrom.

Figure 10C:
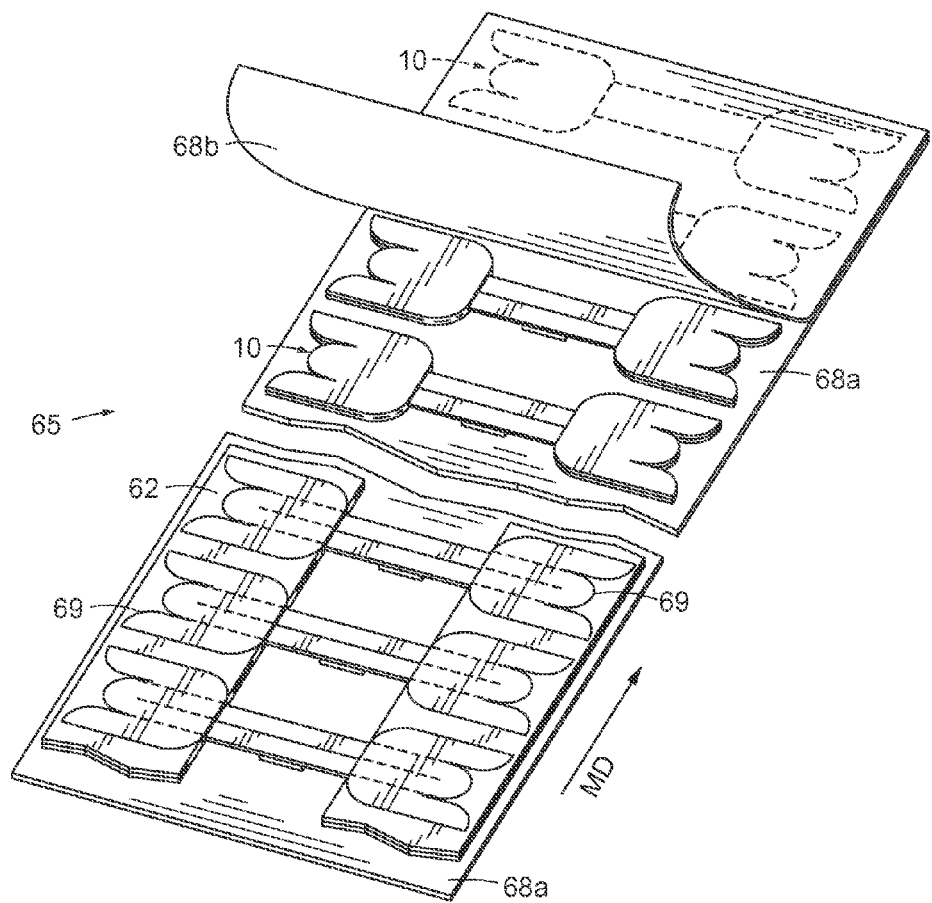
FIG. 10c is a fragmentary perspective view illustrating the final steps of a method of manufacturing the nasal dilator of FIG. 9.

FIG. 10*c* illustrates the final steps of the continuous fabrication process. Fabrication matrix 65 is layered onto one of two packaging film webs, 68*a*, which provides the surface against which individual dilators 10 will be die cut. Die cuts, 69, extend around resilient member end portions 21*a* and 21*b*, as close as practicable thereto, and extend vertically through strands 62, strips 63 and strands 64 to the surface of film web 68*a*. The waste matrix of fabrication matrix 65 is preferably removed leaving finished dilators 10 spaced at equal intervals upon film web 68*a*. In this embodiment, die cuts 69 form end regions 32 and 34 and interface members 16. Die cuts 69 further define the width of interface members 16 extending between the upper and lower long edges of end regions 32 and 34. In this manner interface members 16 simultaneously laminate portions of the base layer of dilator 10 to both the cover layer and resilient layers thereof. Finished dilators are sealed between upper and lower packaging film webs 68*a* and 68*b*. Said webs may be of any suitable material, but are preferably sealable to each other, such as a cohesive cold seal paper film, compression sealable paper film, or heat sealable plastic film.

Figure 11:
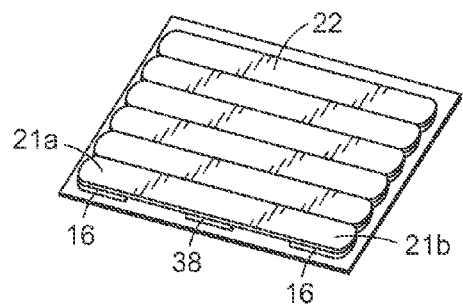
FIG. 11 is a perspective view of a plurality of continuous resilient members as die cut from a continuous resilient layer material.
Figure 12:
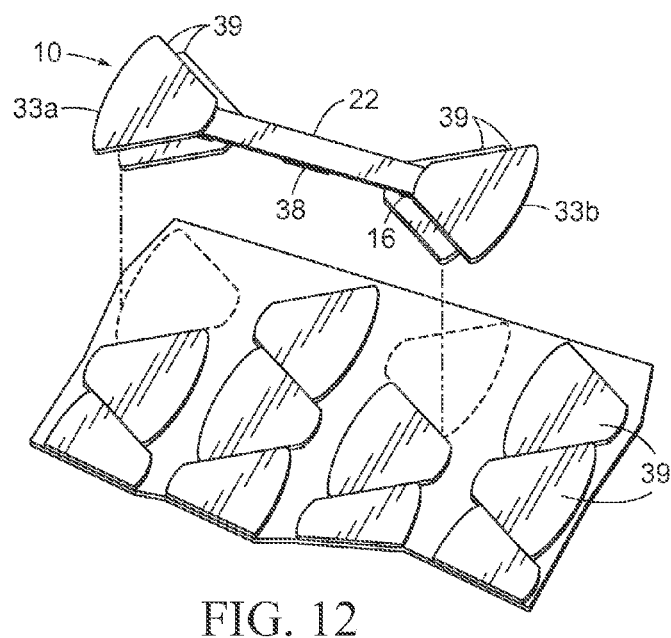
FIG. 12 is a perspective view illustrating a method of manufacturing and assembling the constituent components of a fourth form of nasal dilator embodying the features of the present invention.
Figure 13:
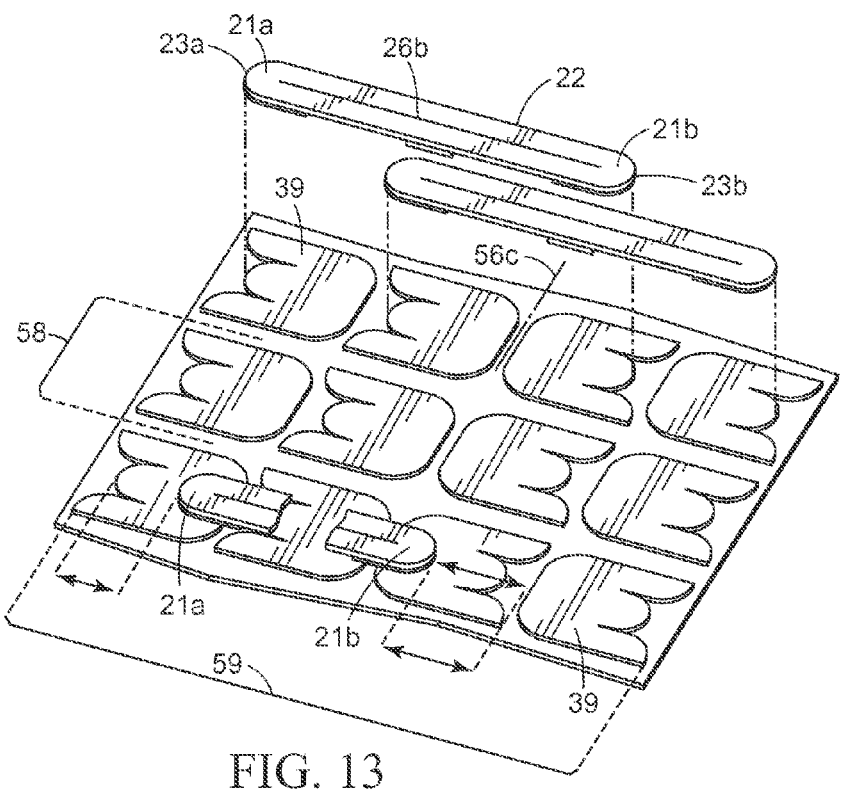
FIG. 13 is a perspective view illustrating a method of manufacturing and assembling the constituent components of an alternate form of the nasal dilator of FIG. 9.

FIGS. 11-13 illustrate embodiments of nasal dilators 10 in accordance with the present invention in which pre-fabricated components are assembled by the user into finished nasal dilator units. FIG. 11 shows a continuous plurality of resilient members 22, die cut from a resilient layer material web 66. Continuous interface material strips 63 and a continuous strand of material from which absorbent pad 38 is fabricated may be laminated to resilient layer material web 66 prior to die cutting finished resilient members 22. Strips 63 are laminated to correspond substantially to resilient member end portions 21a and 21b. The resilient members are die cut, preferably along common lines defining their respective upper and lower longitudinal edges. Said edges may be either perpendicular or parallel to the continuous length (MD) extent of material web 66. Said die cuts are made through resilient material web 66 to the protective paper liner thereof (i.e., kiss cut) to form resilient members 22 including interface members 16 and pads 38. The waste matrix from web 66 is removed from the area surrounding the resilient members, leaving a continuous plurality thereof on said paper liner. Said resilient members may be packaged in groups for retail sale along with base layer and cover layer components of dilator 10.

FIGS. 12 and 13 illustrate continuous rows of end region components die cut from base layer material web 60 using fabrication techniques similar to that described with regard to FIGS. 6-7. The waste matrix from between end region components is preferably removed, leaving said rows on release paper liner. End region components in FIG. 12 are die cut such that they are nested along common lines defining at least a portion of their peripheral edges, and are preferably aligned along their longitudinal centers. End region components in FIGS. 12 and 13 are dimensionally configured, including spacing, if any, between at least a portion of their peripheral edges, such that every other component in each row form a pair. Said pairs correspond substantially to first and second end regions of truss 30 and to the length of dilator 10. The end region components of FIG. 12 are substantially triangular in shape, with a gradient width increasing along their lengths. They may be packaged in groups for retail sale along with resilient layer and cover layer components of dilator 10.

To assemble end region components and resilient members 22 for use on a nose 11, a user removes a resilient member from the paper liner exposing the adhesive substance on at least interface members 16, and affixes end portions 21a and 21b onto a said pair of every other end region components from the continuous plurality thereof, thus substantially forming truss 30. The spaced apart relationship of each pair on paper liners provides a guide as to the length of dilator 10. However, it will be apparent that a slightly greater or lesser length may be selected by the user simply by placing a greater or lesser portion of one end of resilient member 22 onto one component, as desired, lifting said component off the paper liner, and then placing the other end onto another component, as desired. An additional pair of end region components may be peeled by hand from the plurality thereof (i.e., in the same manner one would peel a self-adhesive label from a continuous sheet thereof) and placed on top of each end portion 21a and 21b, aligned with any, all, or none of the peripheral edges of the first pair of end region components underneath resilient member 22. Thus the user may further adjust the overall length and/or width of dilator 10.

A particularly efficacious technique is to align all end region components substantially along the longitudinal centerline of resilient member 22, placing the additional end region components so that they overlap the outer lateral end edges of said first pair of end region components as shown in FIG. 12. The user then applies dilator 10 to a nose 11 in the same way as a prefabricated nasal strip device. In the alternative, a user may successively apply the components of dilator 10, as described above, to nose 11 (i.e., assembly in situ).

Figure 14:
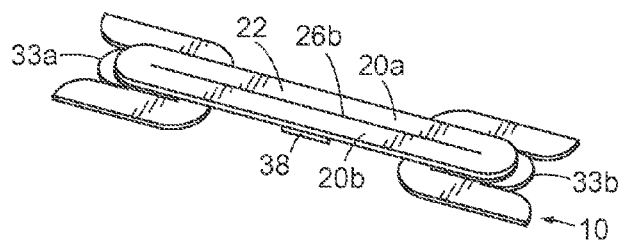
FIG. 14 is a perspective view of a nasal dilator assembled from the components and method illustrated in FIG. 13.

FIG. 13 further illustrates pre-fabricated components of nasal dilator 10 to be assembled by the user. End region components are die cut in a spaced apart grid arrangement, similar to the fabrication techniques described with regard to FIGS. 6-7, comprising rows 58 containing groups 59 centered on line 56c. As similarly described with respect to FIGS. 5-7 and FIG. 12, pairs of components substantially define the length of dilator 10 and/or correspond to the length of resilient member 22. FIG. 13 shows opposite terminal end edges 23a and 23b of resilient member 22 aligning precisely with lateral end edges of end region components. For the sake of clarity, FIG. 13 shows fragmentary sections of resilient member 22 where the user may align end portions 21a and 21b thereof to end region components, preferably within a range as defined by directional arrows in between broken lines, to adjust the length of dilator 10. By example, FIG. 14 illustrates dilator 10 lengthened. A user may also apply one or more additional end region components on top of the embodiment of truss 30 as described with respect to the embodiment of FIG. 12.

A user may be further provided with a variety of disparately sized resilient member components with which to combine with a variety of disparately sized end region components whereby to form any number of nasal dilator configurations, preferably within design parameters for engaging nasal outer walls as discussed hereinbefore. For example, resilient member components with varying degrees of spring biasing force, along with various shapes and configurations of resilient member and end region components may be co-packaged for retail sale. Instructions and suggestions for both routine and optional assembly of said components are easily conveyed to the user within the retail packaging of said components of dilator 10 for retail sale. It will be apparent to the skilled man that the fabrication and assembly techniques for dilator components as disclosed in FIGS. 5-7, 10a-10c, and 11-13 may be applied to a wide variety of nasal dilator devices.

Figure 15:
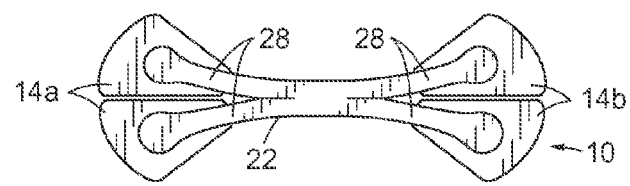
FIG. 15 is a plan view of a fourth form of nasal dilator embodying the features of the present invention.
Figure 16:
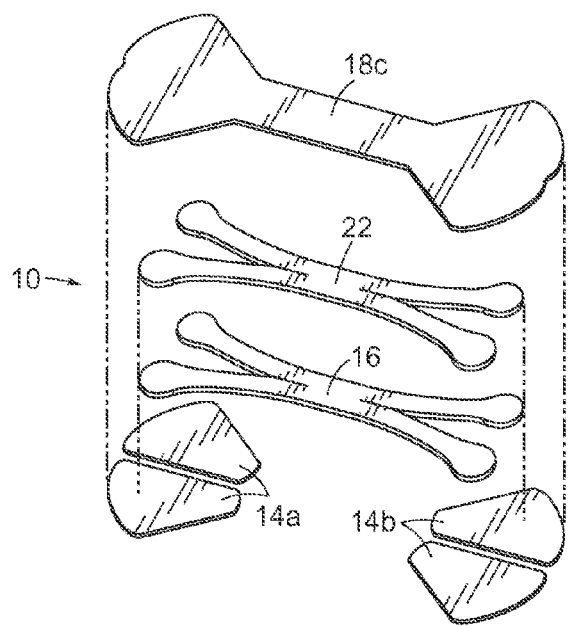
FIG. 16 is an exploded perspective view of an alternative form of the nasal dilator of FIG. 15.

FIGS. 15-16 illustrate an embodiment of nasal dilator 10 in accordance with the present invention in which the discontinuity of material of resilient member 22 comprises a plurality of spring fingers, 28, diverging from a common center and terminating at discrete end region components. Said center is preferably aligned with the lateral and longitudinal centerlines of intermediate region 36 of truss 30. Fingers 28 have gradient widths, and may curve, may be uniform or asymmetric, and may be equidistant from the longitudinal centerline of truss 30 or be of varying distance therefrom. Fingers 28 have enlarged end portions at their terminal ends which engage base layer pads 14a and 14b, respectively, via interface member 16. Said base layer pads are bifurcated laterally into separate components, each engaging each said terminal end of each finger 28. Said separate components may be symmetric or asymmetric, of equal or disparate size and/or shape. This divergent end region structure creates additional lateral torsional flexibility primarily at the end regions of truss 30, and allows dilator 10 to simultaneously engage nasal outer wall tissues adjacent both the nasal valve and nasal vestibule. As further illustrated in FIG. 16, dilator 10 may optionally include a cover layer formed as a single member, 18c, laminated on top of resilient member 22.

Figure 17:
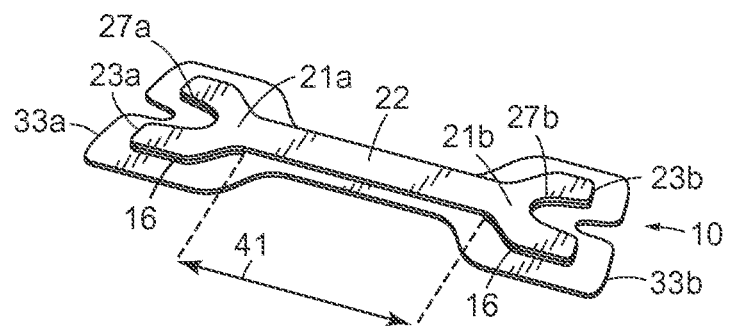
FIG. 17 is a perspective view of a variation of the nasal dilator of FIG. 15.

FIG. 17 illustrates a variation of the embodiment of FIG. 15 in which the discontinuity of material of resilient member 22 comprises indentations, 27a and 27b, extending inward from terminal end edges 23a and 23b thereof forming divergent spring fingers. Said fingers may be confined substantially to the end regions of truss 30, and may be of uniform or non uniform length and width. Said indentations widen resilient member end portions 21a and 21b and help spread the spring biasing force of resilient member 22 laterally from the longitudinal centerline thereof. Lateral end edges 33a and 33b of first and second end regions 32 and 34 are angled inward in a substantially straight line from bottom to top corresponding approximately to the line where nose 11 meets the cheek of a face 12. However, a portion of said lateral end edges may correspond to indentations 27a and 27b. In this particular embodiment, the base layer of dilator 10 is formed as a single member and extends longitudinally through at least portions of the respective regions of truss 30. Said member may also be placed on top of the resilient layer and thus comprise the cover layer of dilator 10, either in addition to or in lieu of said base layer. In the present embodiment, however, interface members 16 adhere the resilient layer to the base layer at the respective end regions of dilator 10, thus creating a separation void, 41, of non-adherence in between said layers which extends between the inside lateral edges of interface members 16. Separation void 41 allows relative independent movement between the base layer and resilient layers of dilator 10 substantially at the intermediate region thereof when dilator 10 is in use on a nose 11.

Figure 18:
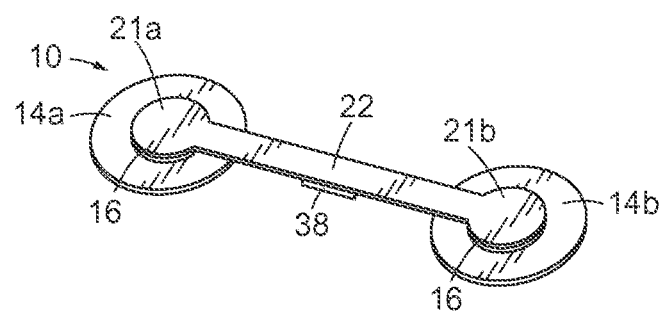
FIG. 18 is a plan view of an alternative form of the nasal dilator of FIG. 4.

FIG. 18 illustrates a variation of the embodiment of FIGS. 12-13 in which the components of dilator 10 may be assembled by the user. FIG. 18 shows resilient member 22 having enlarged, substantially round end portions 21a and 21b corresponding to interface members 16 engaging substantially round base layer pads 14a and 14b, respectively.

As illustrated and described in examples of the preferred embodiments, the components of dilator 10 are fabricated to design parameters suitable for effective engagement to, and dilation of, a nose 11. Said components are simultaneously fabricated with minimal material waste and configured for latitudinal and longitudinal registration to each other. Dilator 10 is further configured to maximize the percentage of a given amount of material used in the manufacturing process and to return a greater number of individual dilator devices per a given quantity of material. Dilator 10 is further configured to facilitate assembly and application by the user, and to allow user adjustment of the truss length.

I claim:
1. A method of fabricating nasal dilator components, comprising the steps of:
 a) die cutting a plurality of first and second end region components configured to dimensions suitable for engaging surface areas of nasal outer wall tissues of a human nose, the plurality of end region components releasably secured to a liner and arranged in a row thereon, the row extending substantially along a y axis centerline and further bisected by an x axis centerline perpendicular thereto, the first end region components on a first side of the x axis and the second end region components on a second side of the x axis; and
 b) die cutting a plurality of resilient members configured to dimensions suitable for providing suitable dilation to surface areas of nasal outer wall tissues of a human nose, the dimensions including a length corresponding at least approximately to a nasal dilator length.

2. The method of claim 1 wherein each first end region component on the first side of the x axis corresponds to one second end region component on the second side thereof, the corresponding first and second end region components each forming a spaced apart pair, the pair substantially defining the length of the nasal dilator.

3. The method of claim 1, further comprising:
 combining the plurality of end region components and resilient members into a kit, the kit configured such that the nasal dilator components can be manually assembled into finished nasal dilator units by an end user.

4. The method of claim 3, further comprising die cutting a plurality of base layer components, each one of the base layer components formed as a single member and releasably secured to a release liner.

5. The method of claim 3, further comprising die cutting a plurality of cover layer components, each one of the cover layer components formed as a single member and releasably secured to a release liner.

6. The method of claim 1 wherein a spaced apart pair of corresponding first and second end region components defines a length of the nasal dilator within a range of from about 1.5" (3.8 cm) to about 3.5" (8.9 cm).

7. The method of claim 1 wherein the plurality of end region components releasably secured to the liner are arranged to correspond to a plurality of different dilator lengths.

8. A method of fabricating a nasal dilator, comprising:
 a) die cutting a plurality of end region components and resilient members, the resilient members die cut laterally adjacent to each other, the resilient members and end region components configured to have a width such that a predetermined non-1:1 ratio of select resilient members align to select end region components substantially along a longitudinal centerline common to the resilient members and the end region components;
 b) aligning the select resilient members to the select end region components; and
 c) bonding at least end portions of the select resilient members to the select end region components.

9. The method of claim 8, further comprising:
 repeating the aligning and bonding operations with non-select end region components and non-select resilient members.

10. The method of claim 8 wherein at least the aligning and bonding operations are performed in a machine direction, the machine direction perpendicular to said common longitudinal centerline.

11. A method of fabricating a nasal dilator, comprising:
 a) slitting a web of end region component material into a plurality of elongated strands;
 b) pairing and separating select, spaced apart strands from the plurality thereof, the paired strands forming a base of a fabrication matrix, the strand widths corresponding at least generally to respective end regions of the dilator, inside edges of each strand from the pair thereof defining, at least in part, inside lateral edges of the first and second end region components, respectively, of the nasal dilator;
 c) die cutting a plurality of resilient members from a resilient layer material web;
 d) forming a fabrication matrix by separating select resilient members from the resilient material web and bonding the select resilient members to the fabrication matrix base at predetermined spaced apart intervals; and e) forming die cuts extending vertically through the fabrication matrix and around end portions of at least some of the bonded resilient members, the die cuts forming the first and second end region components, the die cut end region components interconnected by the bonded resilient members, thus defining finished dilators.

12. The method of claim 11, further comprising:
a) laminating at least one additional strand of end region component material onto the fabrication matrix;
wherein the select strands of end region component material form a dilator base layer; and
the at least one additional strand of end region component material forms a dilator cover layer.

13. The method of claim 12, wherein:
the at least one additional strand of end region component material comprises a pair of cover layer material strands laminated onto the fabrication matrix via their adhesive sides, substantially over the non-adhesive sides of the select spaced apart paired strands, respectively; or
the at least one additional strand of end region component material comprises a single cover layer material strand laminated onto the fabrication matrix substantially over both select spaced apart paired strands and an entire exposed surface of the resilient members bonded thereto.

14. The method of claim 11, further comprising:
a) laminating at least one of a strip of interface material onto one side of the base layer or cover layer material web, such that at least one elongated strand includes an interface material strip laminated thereto.

15. The method of claim 11, further comprising:
a) laminating a strand of absorbent pad material onto one side of the resilient layer material web, the die cutting a plurality of resilient members further extending through the absorbent pad material and forming an absorbent pad on one side of at least a portion of the die cut resilient members.

16. The method of claim 11 wherein the slit web comprises a base layer material, the die cut end region components comprising first and second base layer pads, and further including:
a) laminating at least one of a cover layer material strand onto the fabrication matrix, such that the die cuts further form a cover layer of the dilator, the cover layer comprising discrete first and second cover layer pads or a single cover layer member.

17. The method of claim 11 and further including separating a waste matrix from the fabrication matrix.

18. The method of claim 17 and further including:
a) layering the fabrication matrix onto a first packaging film web, the packaging film web providing a surface against which the nasal dilators are die cut; and
b) layering a second packaging film web onto the fabrication matrix so as to encapsulate the die cut nasal dilators therebetween.

* * * * *